United States Patent
Yang et al.

(10) Patent No.: US 6,444,324 B1
(45) Date of Patent: Sep. 3, 2002

(54) LUBRICATED CATHETER BALLOON

(75) Inventors: Dachuan Yang, Plymouth; Scott L. Sjoquist; Jan D. Seppala, both of Maple Grove, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/727,742

(22) Filed: Dec. 1, 2000

(51) Int. Cl.$^7$ ................................................ B05D 3/10
(52) U.S. Cl. ........................ 428/447; 428/507; 604/265
(58) Field of Search ........................................... 604/265

(56) References Cited

U.S. PATENT DOCUMENTS

| | | | |
|---|---|---|---|
| 4,490,421 A | 12/1984 | Levy | 428/35 |
| 5,344,401 A | * 9/1994 | Radisch et al. | 604/96 |
| 5,348,538 A | 9/1994 | Wang et al. | 604/96 |
| 5,503,631 A | 4/1996 | Onishi et al. | 604/96 |
| 5,509,899 A | 4/1996 | Fan et al. | 604/96 |
| 5,556,383 A | 9/1996 | Wang et al. | 604/96 |
| 5,576,072 A | 11/1996 | Hostettler et al. | 427/532 |
| 5,662,960 A | 9/1997 | Hostettler et al. | 427/2.3 |
| 5,849,368 A | 12/1998 | Hostettler et al. | 427/536 |
| 5,868,704 A | 2/1999 | Campbell et al. | 604/96 |
| 5,902,631 A | 5/1999 | Wang et al. | 427/2.1 |
| 5,919,570 A | 7/1999 | Hostettler et al. | 428/424.8 |
| 6,017,577 A | 1/2000 | Hostettler et al. | 427/2.12 |
| 6,030,656 A | 2/2000 | Hostettler et al. | 427/2.3 |
| 6,040,058 A | 3/2000 | Hostettler et al. | 428/457 |
| 6,080,488 A | 6/2000 | Hostettler et al. | 428/423.3 |
| 6,110,142 A | 8/2000 | Pinchuk et al. | 604/96 |
| 6,120,477 A | 9/2000 | Campbell et al. | 604/96 |
| 6,120,904 A | 9/2000 | Hostettler et al. | 428/423.3 |

OTHER PUBLICATIONS

U.S. application No. 09/306,939, Nazarova et al., filed May 7, 1999.

* cited by examiner

*Primary Examiner*—David W. Wu
*Assistant Examiner*—Caixia Lu
(74) *Attorney, Agent, or Firm*—Vidas, Arrett, & Steinkraus, P.A.

(57) ABSTRACT

A dilatation balloon comprising an inner surface and an outer surface, the inner surface having a lubricious material disposed thereon to reduce friction or prevent adherence of adjacent layers, and thus reduce the pressure required for inflation.

23 Claims, 1 Drawing Sheet

LUBRICATED CATHETER BALLOON

FIELD OF THE INVENTION

The present invention relates to coating the inner surface of a dilatation balloon so as to reduce friction and thus reduce the required opening pressure upon inflation.

BACKGROUND OF THE INVENTION

Medical balloon catheters having a dilatation balloon located at their distal ends, are used surgically for insertion into blood vessels, urethra, or body conduits for the purpose of reducing stenoses or blockages. Conventionally, such catheters are made of materials such as polyamides, nylon, SELAR®, polyesters such as polyethylene terephthalate (PET), polyethylene (PE), polyester elastomers such as HYTREL®, or similar materials. Also, such balloon catheters can be made of several layers with polyethylene terephthalate blended with polyethylene. Also they can be made with blends of polyethylene terephthalate and HYTREL®. HYTREL® is a randomized block co-polymer of polyethers and polyesters. Such materials are not typically by themselves lubricious in nature, and must be rended lubricious by other means such as coating them with a lubricant.

Balloons are typically tightly folded and wrapped upon themselves for delivery to the targeted lesion, storage and are unwrapped and expanded to a size that is considerably greater than the stored size by the introduction of an expansion fluid into the balloon. It is very difficult, and in fact almost impossible, to do so without having portions stick to each other, and possibly tearing the substrate, particularly in the absence of a lubricious coating. Furthermore, this can greatly increase the amount of opening pressure required to inflate the balloon. Or if using for stent delivery, it will need extra pressure to expand the stent and release it.

One method of overcoming some of these issues has been to coat the outside of the balloon in order to reduce the friction between the folded and wrapped layers. This coating can also provide some protection against pinhole formation in the balloon and/or coating by providing surfaces that do not stick to one another. However, coating the outside surface not only adresses the half of the balloon surface for this, but also may lead to what is referred to in the art as "watermelon seeding." This refers to slippage of the balloon wherein the balloon which is too lubricious shoots forward on inflation causing accidental slippage from the target or repair site which ultimately may lead to stent slippage from the target site as well.

It is therefore necessary to also find a way in which the balloon can be retained easily at the target site during expansion or contraction without slippage. This is more readily accomplished when the balloon has no lubricity. One method of overcoming this "watermelon seeding" effect is to make the balloons with both a lubricating portion and a non-lubricating portion. U.S. Pat. No. 5,503,631 to Onishi et al. discloses a vasodilating catheter balloon whose body has a lubricating portion and a non-lubricating portion. The lubricious property of the balloon is created by grafting a lubricious coating onto a non-lubricious substrate. Only the tapered portions on opposite ends of the balloon were treated.

Another method of overcoming the "watermelon seeding" is found in U.S. Pat. No. 6,221,467.

Another issue is that if the lubricant utilized on the outside of the balloon is hydrophobic, it may bead or run off when exposed to an aqueous environment, and can consequently reduce lubricity, and lack abrasion resistance. Hydrophilic coatings are an alternative but can also migrate from the balloon surface in an aqueous environment, particularly if they are water soluble, although there are steps that can be taken to prevent migration from occurring through the use of crosslinking or coupling agents, or binders, for instance.

U.S. Pat. No. 5,509,899 describes a medical balloon and catheter in which the balloon is wrapped and folded upon itself tortuously and tightly so that outer surfaces contact each other for insertion into the body and in which the balloon is free of bridging and adhesion between abutting surfaces. The balloon has a base of a continuous polymeric surface expandable from a folded, wrapped configuration with surfaces touching each other into a balloon when inflated, a lubricious, biocompatible, hydrogel coating disposed on the polymeric surface, and a thin, lubricious, blood-compatible coating disposed upon the hydrogel coating which adheres to it to prevent abutting surfaces of the folded polymeric surfaces from adhering to each other during inflation and to prevent delamination of the hydrogel coating and/or rupture of the balloon.

SUMMARY OF THE INVENTION

The present invention relates to a method of coating the inner surface of the dilatation balloon used with a catheter device with a lubricant in order to overcome friction between surfaces in contact with one another and to consequently reduce the opening pressure required to inflate the balloon. This can also avoid the problem of "water melon seeding".

The dilatation balloon has an inner surface and an outer surface and a lubricious material disposed on the inner surface. The inner surface at least periodically comes into contact with itself. Specifically, dilatation balloons are folded upon themselves for storage. The lubricious material on the inner surface reduces the friction that occurs during inflation of the balloon by reducing or preventing the amount of adhesion occurring between the material of the inner surface as it comes in contact with itself. This lubricious material consequently reduces the opening force required during inflation and thus facilitates an easier inflation. The lubricous material may also reduce pinholeing and ease stent delivery.

DETAILED DESCRIPTIONS OF THE PREFERRED EMBODIMENTS

Figure 1:
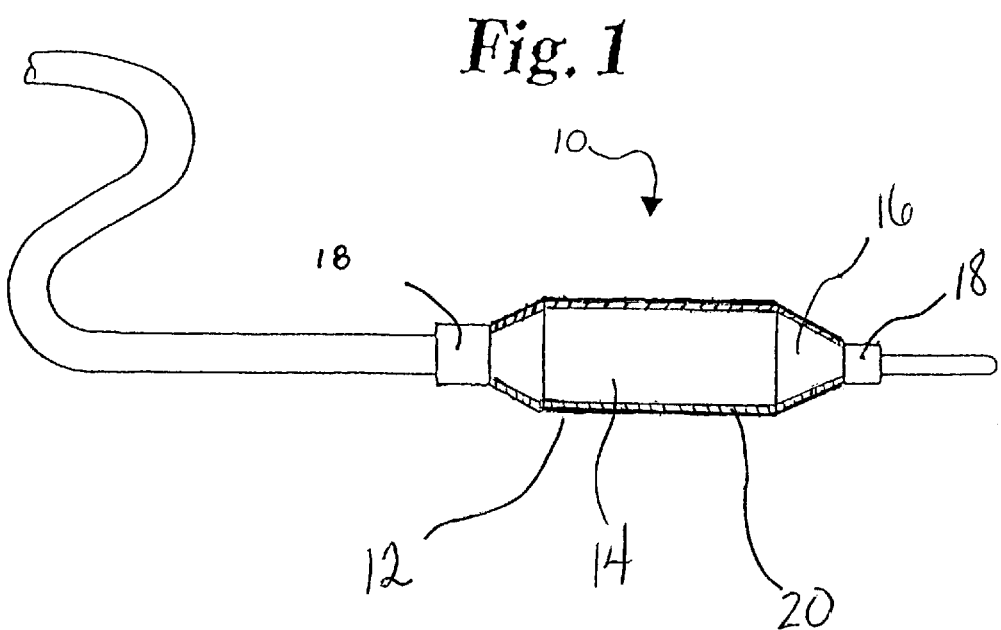
FIG. 1 is a perspective view of a dilatation catheter having a catheter balloon with a lubricous material on its inner surface.

The present invention relates in particular to coating the inner surface of a dilatation balloon with a lubricious material.

Balloons are typically folded and wrapped upon themselves for storage and are unwrapped and expanded to a size that is considerably greater than the stored size by the introduction of an expansion fluid into the balloon. It is very difficult, and in fact almost impossible, to do so without having portions stick to each other, and possibly tearing the substrate, particularly in the absence of a lubricious coating.

FIG. 1 illustrates generally at 10, a dilatation catheter having catheter balloon attached at its distal end shown in its inflated state. Catheter balloon 12 is generally conventional in its structure having a body portion 14, cone portions 16 and waist portions 18. The balloon is characterized in accordance with this invention by having a lubricious material 20 is shown on the inner surfaces of the cone and body portions.

The balloons of the present invention are not limited to any particular any polymeric material, but may be formed of thermoplastic elastomers (i.e. block copolymers), polyolefins such as polyethylene and polypropylene, ethylene α-olefin polymers, polyesters, polyester elastomers, polyamides, polyimides, nylons, polyvinyl chlorides, thermoplastic polyurethanes, polyether-block-amide copolymers, ionomeric polymers, and their copolymers, and so forth. The term copolymer will be hereinafter used to refer to those polymers having three (terpolymers) or more different monomers as well as two.

More specifically, materials such as nylon; SELAR®; polyether-polyester block copolymers such as HYTREL®; polyether block amide copolymers such as PEBAX® including PEBAX® 7033 or 7233; polyester block ethers such as ARNITEL® including ARNITEL® EM 40; SURLYN® ionomeric polymers such as ethylene/methacrylic acid (E/MAA) copolymers wherein the MAA acid groups have been partially neutralized with lithium, sodium, or zinc ions; polyethylene terephthalate (PET); polytetrafluoroethylene (PTFE); polyvinyl chloride; polyethereurethanes; polyesterurethanes; polyurethane ureas; polyurethane siloxane block copolymers; silicone polycarbonate copolymers; ethylene vinyl acetate copolymers; acrylonitrile-butadiene-styrene copolymers; polyphenylene sulfides; copolyesters; copolymers thereof; or other similar extrudable thermoplastic, polymeric materials, or composites thereof may be utilized in the present invention. Thermosetting materials such as polyimides may also be utilized.

The formation of catheter balloons made of block copolymer elastomers where the hard segments are polyester or polyamide and the soft segments are polyether, is discussed in U.S. Pat. No. 5,556,383 issued Sep. 17, 1996 to Wang et al. incorporated by reference herein.

Some balloon materials which may be preferable for use include, but are not limited to, the polyether block amides, such as PEBAX® 7033 or 7233; the polyester block ethers such as ARNITEL® EM 40; PET; and nylon.

Balloon formation may be carried out in any conventional manner with conventional extrusion and blowing techniques, but basically there are three major steps in the process which include extruding a tubular preform, blow molding the balloon and annealing the balloon. Depending on the balloon material employed, the preform may be axially stretched before it is blown. Techniques for balloon formation are discussed in U.S. Pat. No. 4,490,421 to Levy and in U.S. Pat. No. 5,348,538 issued Sep. 20, 1994 to Wang et al.

The lubricious materials that may be utilized to lubricate the inner surface of the dilatation balloons include both hydrophobic and hydrophilic materials. These materials may be crosslinked or reactive compounds, or they may be non-reactive or uncrosslinked compounds, and may include those that are actually coupled to the balloon surface through the use of a coupling agents, for instance.

Useful hydrophobic materials include both reactive and nonreactive compounds. Some examples include, but are not limited to, glycerine, olive oil, vegetable-oil, peanut oil, and so forth.

Other hydrophobic materials found to be quite useful include silicones (i.e. organosiloxane polymers), functionalized silicones, hydrolyzable silanes which form silicones, fluorosilanes, and so forth, or mixtures thereof. These compounds Include both reactive and non-reactive species including those that are crosslinkable in the presence of moisture. Blends of these compounds also find utility herein.

For instance, a blend of a hydrolyzable siloxane, such as an amino terminated siloxane, and a non-crosslinkable silicone oil is useful such as a blend of an amino terminated hydrolyzable polydimethylsiloxane (PDMS) and a nonhydrolyzable polydimethylsiloxanes. The noncuring (i.e. nonhydrolyzable) PDMS acts as a plasticizer which may cause the hydrolyzable PDMS to swell, forming a gel-like substance. Sesame oil and other natural oils can also be used as a plasticizer.

Other examples of useful hydrolyzable silanes or siloxanes include, but are not limited to, 1-methoxy-3-(trimethylsiloxy)butadiene; methyltrimethoxysilane; triphenylsilanol; 1,1,3,3-tetramethyl-1,3-diethoxydisiloxane; triethylacetoxysilane; and so forth. These reactive compounds include terminal groups that are activated by moisture. Such terminal groups include, but are not limited to, $C_1$ to $C_{12}$ alkoxy groups, in particular the lower $C_1$ to $C_4$ alkoxy groups such as methoxy or ethoxy, $C_2$ to $C_4$ acyloxy, up to about $C_6$ (poly)alkoxyalkoxy, phenoxy, amine, oxime, halogen groups including chlorine, fluorine and bromine, and so forth. In particular emodiments of the present invention, hydrolyzable groups including the alkoxy, alkoxyalkoxy and the acyloxy groups are used.

Other hydrophobic materials useful herein include cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, polyacetal, nylon, polyester, styrene-butadiene copolymers, acrylic resin, polyvinylidene chloride, polycarbonate, homopolymers and copolymers of vinyl compounds, polyvinylchloride, Hydrophilic materials also find utility in the present invention. Some examples of useful hydrophilic compounds include, but are not limited to, homopolymers and copolymers of N-vinyllactam including N-vinylpyrrolidone, N-butyrolactam, N-vinyl caprolactam, polyvinylpyrrolidone, polyvinyl acetate copolymers, polyethers, polysaccharides, hydrophilic polyurethanes, acrylates such as polyacrylates and polymethacrylates having hydrophilic esterifying groups, polyhydroxyacrylate, poly(acrylic acid), poly(acrylamides), poly(N-alkylacrylamide), poly(vinyl alcohols), poly(acrylates), poly (methacrylates), poly(vinyl esters), poly(maleate esters), poly(fumarate esters), poly(ethyleneimines), polyamides, ionomeric polymers, vinyl compounds having hydrophilic polar pendant groups, and natural polymers including collagen, poly(saccharides), cellulose, methyl cellulose, carboxymethylcellulose, hydroxypropyl cellulose, polyvinylsulfonic acid, heparin, dextran, modified dextran, xanthan, chondroitin sulphate, lecithin, and so forth, and mixtures thereof.

The hydrophilic lubricious materials also include both reactive and non-reactive species.

Particularly useful hydrophilic materials include hydrogels, homopolymers and copolymers of polyalkylene oxides or alkoxypolyalkylene oxides, and homopolymers or copolymers of at least one polymerizable ethylenically unsaturated compound.

The polyalkylene oxides of alkoxy polyalkylene glycols include, in particular, polyethylene glycol, polyethylene oxide/polypropylene oxide (EO/PO) block copolymers, or mixtures thereof. The copolymer of polyethylene oxide/castor oil, for instance, so called Cremophor®'s, e.g. Cremophor EL also are very good hydrophilic lubricant materials.

The homopolymers and copolymers of the polymerizable ethylenically unsaturated compound include polycarboxylic acids, including homopolymers or copolymers of acrylic acid, (meth)acrylic acid, fumaric acid, maleic acid, maleic anhydride, and so forth. Other ethylenically unsaturated compounds are those having vinyl groups, and diene compounds.

Copolymers of maleic acid may be obtained by the maleic anhydride copolymer by reaction of some of the anhydride groups with an inorganic hydroxide, water, monofunctional amine, alcohol, epoxy, imine, and so forth, or some mixture thereof. Such maleic anhydride copolymers include poly (ethylene-maleic anhydride) and maleic anhydride/methyl vinyl ether. These types of lubricious materials are discussed in U.S. Pat. No. 5,902,631 incorporated by reference herein in its entirety.

The hydrogels are typically hydrophilic in nature and typically have the ability to dissolve or swell in an aqueous environment, and are capable of manifesting lubricity while in a wet state. When hydrated, these polymers exhibit low frictional forces forces in humoral fluids such as saliva, digestive fluids and blood, as well as in saline solution and water. One particular example of a hydrogel is an interpenetrating network (IPN) of a hydrogel of polyethylene oxide (PO) captured in a crosslinked acrylic polymer network. This IPN is formed by polymerizing a mixture of an acrylic monomer composition comprising a monomer having plural (meth)acrylate groups and polyethylene oxide.

Other polymeric materials which hydrogels may comprise include polyethylene oxides in interpenetrating networks with poly(meth)acrylate homopolymers or copolymers; copolymers of maleic anhydride; (meth)acrylamide homopolymers and copolymers; (meth)acrylic acid copolymers; poly(vinyl pyrrolidone) and blends or interpolymers with polyurethanes; polysaccharides, and so forth.

Hydrogels are discussed, for instance, in U.S. Pat. Nos. 6,120,904, 6,080,488, 6,040,058, 6,030,656, 6,017,577, 5,919,570, 5,849,368, 5,662,960, and 5,576,072 all of which are incorporated by reference herein in their entirety.

Alternatively, the lubricious coatings can be formed from hydrophobic compounds which can be converted to a lubricious hydrophilic compound through a chemical reaction such as hydrolysis, for instance. The conversion may take place once the coating process is complete. Examples of such compounds include those compounds having pendant ester or amide groups, such as, for instance, esters such as poly(acrylates), poly(meth)acrylates, poly(vinyl esters), poly(maleates), poly(fumerates), polyamides, poly (acrylamides), and copolymers and terpolymers thereof, and so forth. The poly(acrylic), poly(methacrylic) or polymaleic esters, and the polyamides or poly(acrylamides) may be converted to carboxylic acids by hydrolysis. Hydrolysis may be basic or acidic, and heat may be added to increase the rate of reaction. Esters are hydrolyzed reversibly in the presence of acid or irreversibly in the presence of base. The use of a large excess of water in the acid-catalyzed reaction favors hydrolysis. Vinyl esters may also be converted to an alcohol through saponification using an alkali-metal hydroxide which forms the alcohol and the metal salt of the acid. While most of these materials are hydrophobic, some are hydrophilic and can be hydrolyzed as well While the above lubricious materials exemplify the present invention, they are not intended as a limitation on the scope of the present invention. Providing the materials are lubricious, they will find utility as a lubricant on the inner surface of the dilatation balloons of the present invention.

The lubricious materials may be dissolved in a solvent or a cosolvent mixture prior to application to a balloon preform, for instance, using any conventional coating techniques such as injecting, dipping, spraying, brushing, and so forth. A preferable method for coating is injecting the coating solution into the tubular device.

Useful solvents include alcohols, aliphatic hydrocarbons, aromatic hydrocarbons, chlorinated solvents, esters, glycols, ethers, glycol ethers, ketones, and so forth. Polar solvents include alcohols, glycols, water and so forth. Specific examples include ethanol, methanol, isopropanol, stearyl alcohol, ethylene glycol, propylene glycol, glycerin, water and so forth. Non-polar solvents include aliphatic hydrocarbons such as heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits and so forth.

Particularly preferred solvents, particularly for the hydrophilic coatings, include ethers, alcohols, water, and their mixtures.

For hydrophilic coatings, the preferable solvents are more polar and preferably include the alcohols such as isopropyl alcohol or isopropanol and water and mixtures thereof. A 1–20% solution of lubricious polymer is preferably utilized and more preferably a solution of about 3% to about 10 wt-% of the polymer is used.

The coating thickness, once the solvent has evaporated, is preferably from about 1 to about 10 μm, more preferably from about 2 to about 6 μm and most preferably from about 2 to about 4 μm. The solvent may be allowed to evaporate at ambient temperatures or the tubing may be dried. The pressured air or vacuum may also be used to speed the drying. In case reactive coating material used a moisture air stream can be passed through under room or elevated temperature to help the curing or crosslinking.

The lubricious material may be applied to the balloon by using a solution of the lubricious material in solvent, and injecting the solution through a tubular preform, or by spraying the preform prior to blowing the balloon. The lubricious material may also be coextruded with the tubular preform. The balloon or tubular preform may also be dipped in a solution of the lubricious material. There are various other means of applying the lubricious material to the inner surface of the balloon material.

The above embodiments are illustrative of the present invention, and are not intended to limit the scope of the present invention.

What is claimed is:

1. A dilatation balloon comprising an inner surface and an outer surface said inner surface having a lubricious hydrophilic material disposed thereon.

2. The dilatation balloon of claim 1 wherein said balloon comprises a thermoplastic polymeric material.

3. The dilatation balloon of claim 2 wherein said thermoplastic polymeric material is selected from the group consisting of thermoplastic elastomers, polyolefins, ethylene-α-olefn polymers, polyesters, polyester elastomers, polyamides, polyimides, nylons, polyvinyl chlorides, thermoplastic polyurethanes, ionomeric polymers and mixtures thereof.

4. The dilatation balloon of claim 2 wherein said thermoplastic polymeric material is selected from the group consisting of polyethyleneterephthalates, polyether-block amide copolymers, polyether-polyester block copolymers, polyester block ether copolymers, ethylene/methacrylic acid copolymers, polytetrafluoroethylenes, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers, polyphenylene sulfides, and mixtures thereof.

5. A dilatation balloon comprising an inner surface and an outer surface said inner surface having a lubricious material comprising a hydrophobic compound selected from the group consisting of hydrophobic cellulose compounds, vinyl compounds, polyvinylchlorides, polyvinylchloride acetates, polyvinylidene chlorides, polyacetals, nylons, polyesters, styrene-butadiene copolymers, acrylic resins, polycarbonates, natural rubber, copolymers thereof, and mixtures thereof.

6. The dilatation balloon of claim 1 wherein said lubricious material comprises at least one selected from hydrogels, homopolymers and copolymers of polyalkylene oxides or alkoxypolyalkylene oxides, homopolymers or copolymers of at least one polymerizable ethylenically unsaturated compound, or mixtures thereof.

7. The dilatation balloon of claim 6 wherein said lubricious material is a polyethylene glycol, an ethylene oxide/propylene oxide block copolymer, a polyethylene oxide/castor oil copolymer, or mixture thereof.

8. The dilatation balloon of claim 1 wherein said lubricious material comprises at least one selected from the group consisting of collagen, poly(saccharides), cellulose, methyl cellulose, carboxymethylcellulose, polyvinylsulfonic acid, heparin, dextran, modified dextran, chondroitin sulphate, lecithin, poly(vinylpyrrolidone), poly(vinyl alcohol), poly(acrylates), poly(methacrylates), poly(fumarate esters), poly(vinyl esters), poly(maleate esters), poly(acrylamide), poly(N-acrylamide), poly(ethyleneimine), polyamides, ionomeric polymers, copolymers thereof, and mixtures thereof.

9. The dilatation balloon of claim 1 wherein said lubricious material comprises at least one polycarboxylic acid.

10. The dilatation balloon of claim 9 wherein said polycarboxylic acid comprises at least one carboxylic acid selected from maleic acid, fumaric acid, acrylic acid, and (meth)acrylic acid.

11. The dilatation balloon of claim 6 wherein hydrogel comprises a polyethylene oxide captured in an interpenetrating crosslinked acrylic polymer network.

12. The dilatation balloon of claim 6 wherein said hydrogel comprises polyethylene oxide in an interpenetrating network with poly(meth)acrylate polymers or copolymers; copolymers of maleic anhydride; (meth)acrylamide polymers and copolymers; (meth)acrylic acid copolymers; poly(vinyl pyrrolidone) and blends or interpolymers with polyurethanes; and polysaccharides.

13. The dilatation balloon of claim 1 wherein said lubricious hydrophilic material comprises at least one hydrophilic polyurethane.

14. A dilatation balloon comprising an inner surface and an outer surface said inner surface having a lubricious material comprising at least one silicone, functionalized silicone, hydrolyzable silane which forms a silicone, fluorosilane, or mixture thereof disposed thereon.

15. The dilatation balloon of claim 14 wherein said lubricious material comprises a hydrolyzable silane having terminal groups selected from $C_1$ to $C_{12}$ alkoxy, $C_2$ to $C_4$ acryloxy, up to about $C_6$(poly)alkoxyalkoxy, phenoxy, amine, oxime, chlorine, fluorine, and bromine.

16. The dilatation balloon of claim 14 wherein said lubricious material comprises at least one hydrolyzable siloxane and at least one nonhydrolyzable siloxane.

17. The dilatation balloon of claim 16 wherein said lubricious material comprises at least one amino terminated hydrolyzable polydimethylsiloxane and at least one nonhydrolyzable polydimethylsiloxane.

18. The dilatation balloon of claim 1 wherein said lubricious material comprises at least one copolymer of maleic acid.

19. The dilatation balloon of claim 18 wherein said copolymer of maleic acid is derived from a maleic anhydride copolymer modified by reaction of some of the anhydride groups thereof with a member selected from the group consisting of inorganic hydroxides, water, monofunctional amines, alcohols, epoxies, imines, and mixtures thereof.

20. The dilatation balloon of claim 19 wherein said maleic anhydride copolymer is a poly(ethylene-maleic anhydride) copolymer or a maleic anhydride-methyl vinyl ether copolymer.

21. A dilatation balloon comprising an inner surface wherein said inner surface is at least occasionally subjected to contact with itself, said inner surface having a lubricious hydrophilic material disposed thereon to reduce the friction when said inner surface comes in contact with itself.

22. A dilatation balloon comprising an inner surface wherein said inner surface is at least occasionally subjected to contact with itself, said inner surface having a lubricious material comprising at least one silicone, functionalized silicone, hydrolyzable silane which forms a silicone, fluorosilane, or mixture thereof disposed thereon to reduce the friction when said inner surface comes in contact with itself.

23. A dilatation balloon comprising an inner surface and an outer surface said inner surface having a lubricious material comprising a hydrophobic compound having hydrolyzable pendant ester or amide groups selected from poly(acrylates), poly(meth)acrylates, poly(vinyl esters), poly(maleates), poly(fumerates), polyamides, poly(acrylamides), and mixtures thereof.

* * * * *